(12) United States Patent
Suzuki et al.

(10) Patent No.: US 9,006,262 B2
(45) Date of Patent: Apr. 14, 2015

(54) THERAPEUTIC OR PROPHYLACTIC AGENT FOR CACHEXIA

(75) Inventors: Tomohiko Suzuki, Kamakura (JP); Yoshitaka Yoshizawa, Kamakura (JP); Mikito Hirakata, Kamakura (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 13/982,578

(22) PCT Filed: Jan. 30, 2012

(86) PCT No.: PCT/JP2012/051937
§ 371 (c)(1),
(2), (4) Date: Jul. 30, 2013

(87) PCT Pub. No.: WO2012/105475
PCT Pub. Date: Aug. 9, 2012

(65) Prior Publication Data
US 2013/0310414 A1 Nov. 21, 2013

(30) Foreign Application Priority Data
Jan. 31, 2011 (JP) .................. 2011-018021

(51) Int. Cl.
*A61K 31/44* (2006.01)
*A61K 31/485* (2006.01)
(52) U.S. Cl.
CPC .................... *A61K 31/485* (2013.01)
(58) Field of Classification Search
CPC .................... A61K 31/485
USPC ......................................... 514/289
See application file for complete search history.

(56) References Cited

FOREIGN PATENT DOCUMENTS

| JP | 05-043466 A | 2/1993 |
|---|---|---|
| JP | 2000-053572 A | 2/2000 |
| JP | 2000-095685 A | 4/2000 |
| JP | 2001-163784 A | 6/2001 |
| JP | 2011-074018 A | 4/2011 |
| WO | 93/15081 A1 | 8/1993 |
| WO | 95/01178 A1 | 1/1995 |
| WO | 95/03307 A1 | 2/1995 |
| WO | 98/23290 A1 | 6/1998 |
| WO | 98/51329 A1 | 11/1998 |
| WO | 99/05146 A1 | 2/1999 |
| WO | 99/11289 A1 | 3/1999 |
| WO | 01/14383 A1 | 3/2001 |
| WO | 02/066475 A2 | 8/2002 |
| WO | 02/078744 A1 | 10/2002 |
| WO | 02/089845 A1 | 11/2002 |
| WO | 2005/097261 A1 | 10/2005 |
| WO | 2006/095836 A1 | 9/2006 |
| WO | 2008/133297 A1 | 11/2008 |
| WO | 2009/001764 A1 | 12/2008 |
| WO | 2009/044883 A1 | 4/2009 |
| WO | 2011/009015 A1 | 1/2011 |
| WO | 2011/009020 A2 | 1/2011 |
| WO | 2011/093441 A1 | 8/2011 |

OTHER PUBLICATIONS

Juhani Lahdevirta, M.D. et al., "Elevated levels of circulating cachectin/tumor necrosis factor in patients with acquired immunodeficiency syndrome," The American Journal of Medicine, vol. 85, 1988, pp. 289-291 (Abstract only).
K.A. Kern et al., "Cancer cachexia," Journal of Parenteral and Enteral Nutrition, vol. 12, No. 3, May 1, 1988, pp. 286-298 (Abstract only).
K.A. Nelson et al., "The cancer anorexia-cachexia syndrome," Journal of Clinical Oncology, vol. 12, No. 1, Jan. 1994, pp. 213-225 (Abstract only).
Takeshi Sagara et al., "Design and synthesis of 10-oxo derivative of N-cyclopropylmethyl (−)-6β-acetylthiodihydro-normorphine, a potentially κ-selective opioid receptor ligand," Bioorganic & Medicinal Chemistry Letters, vol. 5, Issue 14, Jul. 20, 1995, pp. 1505-1508 (Abstract only).
Michael J. Tisdale, "Biology of Cachexia," Journal of the National Cancer Institute, vol. 89, Issue 23, 1997, pp. 1763-1773 (Abstract only).
Hiromasa Horikiri et al., "A Convenient Oxidation Method of the Benzylic 10-Position in 4,5-Epoxymorphinan," Heterocycles, vol. 63, No. 4, 2004, pp. 865-870 (Abstract only.
H. Horikiri et al., "Syntheses of 10-oxo, 10 alpha-hydroxy, and 10 beta-hydroxy derivatives of a potent kappa-opioid receptor agonist, TRK-820," Chem. Pharm. Bull. (Tokyo), vol. 52, No. 6, Jun. 2004, pp. 664-669 (Abstract only).
Masanori Fukushima, Merck Manual, 18th Edition, Japanese language edition, Nikkei Business Publications, Inc., 2007, p. 1234 with translation.

*Primary Examiner* — Kevin E Weddington
(74) *Attorney, Agent, or Firm* — DLA Piper LLP (US)

(57) ABSTRACT

A therapeutic or prophylactic agent for cachexia includes as an effective ingredient a compound having a specified morphinan skeleton represented by a compound of the following structure:

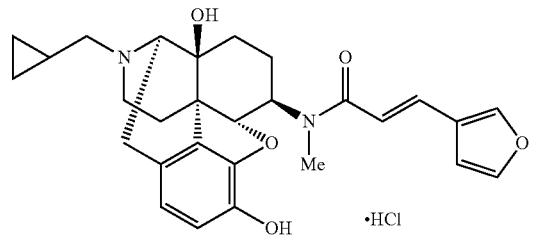

or a pharmacologically acceptable acid addition salt thereof.

8 Claims, 1 Drawing Sheet

THERAPEUTIC OR PROPHYLACTIC AGENT FOR CACHEXIA

TECHNICAL FIELD

This disclosure relates to a therapeutic or prophylactic agent for cachexia comprising as an effective ingredient a compound having a morphinan skeleton or a pharmacologically acceptable acid addition salt thereof.

BACKGROUND

Cachexia, also referred to as cachexy, is a systemic syndrome having major symptoms such as remarkable body weight loss, anemia, edema, anorexia, general prostration, malaise and the like in chronic diseases such as malignant tumor, tuberculosis, diabetes, blood diseases, endocrine disorders, infections, acquired immunodeficiency syndrome and the like (J. Parenteral and Enteral Nutrition, 12, 286-298 (1988) and Am. J. Med., 85, 289-291 (1988)).

Among those kinds of cachexia, a particular kind of cachexia caused by malignant tumor, that is, cancer cachexia is often observed, and cancer cachexia is said to account for about 20% of the deaths from malignant tumor (J. Natl. Cancer Inst., 89, 1763-1773 (1997)). In cancer cachexia, the progression of cachexia significantly weakens the physical strength of patients, and thus it does not allow the patients to be treated with antitumor agents, which are generally highly toxic, and it seriously undermines the treatment of malignant tumors. Furthermore, nutritional support to ameliorate the symptoms of cachexia can conversely lead to exacerbation of malignant tumor, reduced quality of life (QOL) of the patient and decreased lifetime. Moreover, in cases of cancer cachexia, administration of an antitumor agent may induce antitumor effects, but the administration, in most cases, rather causes side effects of the antitumor agents such as bone marrow toxicity and the like, and thus cachexia is not ameliorated (J. Clin. Oncol., 12, 213-225 (1994)).

Up to this point, as a substance having an ameliorating effect on cachexia, 1,2-diphenylpyrrole derivatives (JP 2000-095685 A), carboxylic acid amide derivatives (JP Hei 5-043466 A), parathyroid hormone-related peptide antibodies (WO 98/051329), ghrelin-like small molecule compounds (WO 05/097261), androgen receptor modulators (WO 02/066475) and the like are known. Even now, however, the pathogenesis of cachexia is unclear, and no agent is effective enough to be clinically used as a therapeutic agent for cachexia.

Meanwhile, a compound having a morphinan skeleton or a pharmacologically acceptable acid addition salt thereof has been disclosed to have an agonistic activity on the kappa opioid receptor, and the uses as an analgesic and a diuretic have been disclosed (WO 93/015081). Furthermore, the uses of the compound or the acid addition salt as an antitussive (WO 95/001178), a brain cell protecting agent (WO 95/003307), an antipruritic (WO 98.023290), a therapeutic agent for hyponatremia (WO 99/005146), an ORL-1 receptor antagonist (JP 2000-053572 A), a therapeutic agent for neuropathic pain (WO 01/014383), an antipruritic for cornea or conjunctiva (JP 2001-163784 A), a therapeutic agent for neuropsychiatric disorder (WO 02/078744), a therapeutic agent for drug dependence (WO 99/011289), a therapeutic agent for septicemia (WO 02/089845), a therapeutic agent for multiple sclerosis-associated pain (WO 06/095836), a therapeutic agent for schizophrenia (WO 09/001764), a therapeutic agent to improve skin conditions (WO 09/044883) and a therapeutic agent for dyskinesia (WO 08/133297) have been disclosed and, though published after the priority date of this application, the uses of the compound or the acid addition salt as a therapeutic agent for fibromyalgia (JP 2011-074018 A) and a therapeutic agent for biliary tract disease (WO 11/093441) have also been disclosed. However, the therapeutic or prophylactic effect thereof for cachexia has not been disclosed at all.

It could therefore be helpful to provide a therapeutic or prophylactic agent for cachexia which comprises as an effective ingredient a compound having a morphinan skeleton or a pharmacologically acceptable acid addition salt thereof and is capable of preventing or ameliorating the progression of symptoms of cachexia.

SUMMARY

We discovered that a specific compound having a morphinan skeleton or a pharmacologically acceptable acid addition salt thereof has an excellent therapeutic or prophylactic effect on cachexia.

That is, we provide the following [1] to [5]:

[1] A therapeutic or prophylactic agent for cachexia comprising as an effective ingredient a compound of Formula (I):

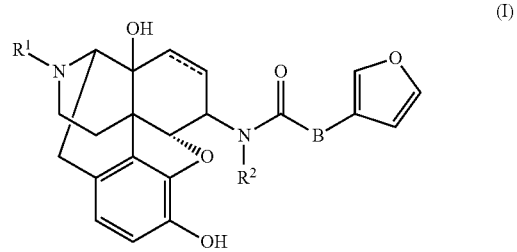

wherein a double line consisting of a broken line and a solid line represents a double bond or single bond, $R^1$ represents $C_4$-$C_7$ cycloalkylalkyl, $R^2$ represents $C_1$-$C_5$ linear or branched alkyl, and B represents —CH=CH— or a pharmacologically acceptable acid addition salt thereof.

[2] The therapeutic or prophylactic agent for cachexia according to [1], wherein, in Formula (I), $R^1$ is cyclopropylmethyl, cyclobutylmethyl, cyclopentylmethyl or cyclohexylmethyl, and $R^2$ is methyl, ethyl or propyl.

[3] The therapeutic or prophylactic agent for cachexia according to [1], wherein, in Formula (I), $R^1$ is cyclopropylmethyl, $R^2$ is methyl, and B is —CH=CH— in trans-form.

[4] The therapeutic or prophylactic agent for cachexia according to [1], wherein the compound represented by Formula (I) is (−)-17-(cyclopropylmethyl)-3,14β-dihydroxy-4,5α-epoxy-6β-[N-methyl-trans-3-(3-furyl)acrylamido]morphinan:

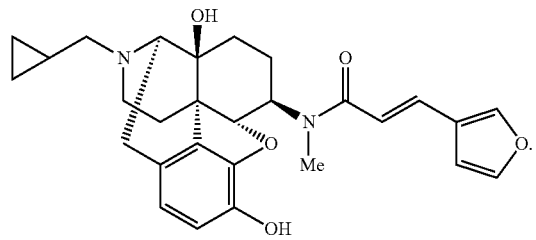 [SMILES: CN(C(=O)/C=C/c1ccoc1)[C@@H]1CC[C@@]2(O)[C@H]3Cc4ccc(O)c5c4[C@@]2(CCN3CC2CC2)[C@H]1O5]

[5] The therapeutic or prophylactic agent for cachexia according to any one of [1] to [4], wherein the cachexia is cancer cachexia.

Our therapeutic or prophylactic agent for cachexia thus comprises as an effective ingredient the compound having a morphinan skeleton or a pharmacologically acceptable acid addition salt thereof. The therapeutic or prophylactic agent ameliorates a systemic syndrome having major symptoms such as remarkable body weight loss, anemia, edema, anorexia, general prostration, malaise and the like in chronic diseases.

DETAILED DESCRIPTION

Figure 1:
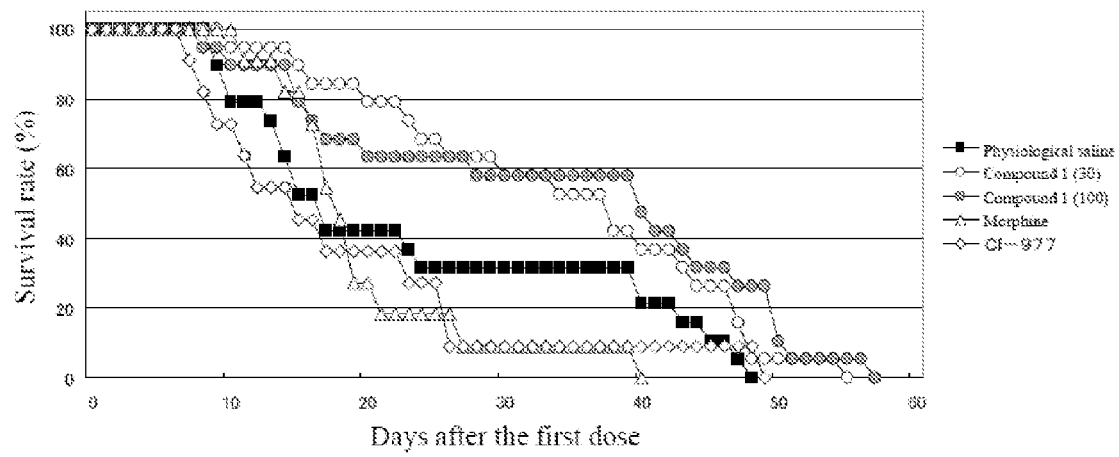
FIG. 1 shows the therapeutic effect of Compound 1 on cachexia (life-prolonging effect).

Our therapeutic or prophylactic agent for cachexia comprises as an effective ingredient a compound of Formula (II):

(II)

wherein the double line consisting of a broken line and a solid line represents a double bond or single bond;
$R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, furan-2-ylalkyl (wherein the number of carbon atoms in the alkyl moiety is 1 to 5) or thiophen-2-ylalkyl (wherein the number of carbon atoms in the alkyl moiety is 1 to 5);
$R^{14}$ represents hydrogen, hydroxy, nitro, $C_1$-$C_5$ alkanoyloxy, $C_1$-$C_5$ alkoxy, $C_1$-$C_5$ alkyl or $NR^9R^{10}$ (wherein $R^9$ represents hydrogen or $C_1$-$C_5$ alkyl, and $R^{10}$ represents hydrogen, $C_1$-$C_5$ alkyl or —(C=O)$R^{11}$ (wherein $R^{11}$ represents hydrogen, phenyl or $C_1$-$C_5$ alkyl));
$R^3$ represents hydrogen, hydroxy, $C_1$-$C_5$ alkanoyloxy or $C_1$-$C_5$ alkoxy;
A represents —XC(=Y)—, —XC(=Y)Z—, —X— or —XSO$_2$— (wherein X, Y and Z each independently represent $NR^4$, S or O (wherein $R^4$ represents hydrogen, $C_1$-$C_5$ linear or branched alkyl, or $C_6$-$C_{12}$ aryl, and, in cases where two or more $R^4$ exist in the formula, these may be the same or different));
B represents a valence bond, $C_1$-$C_{14}$ linear or branched alkylene (which may be substituted by at least one or more kinds of substituents selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy; and whose 1 to 3 methylenes may be substituted by carbonyl), $C_2$-$C_{14}$ linear or branched unsaturated non-cyclic hydrocarbon containing 1 to 3 double bonds and/or triple bonds (which may be substituted by at least one or more kinds of substituents selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy; and whose 1 to 3 methylenes may be substituted by carbonyl), or $C_1$-$C_{14}$ linear or branched, saturated or unsaturated hydrocarbon containing 1 to 5 thioether bonds, ether bonds and/or amino bonds (wherein no heteroatom is bound directly to A, and 1 to 3 methylenes thereof may be substituted by carbonyl);
$R^5$ represents hydrogen or an organic group having any of the following basic skeletons:

Q: N, S, O
T: CH$_2$, NH, S, O
l = 0-5
m, n ≥ 0
m + n ≤ 5 wherein Q represents N, O or S; T represents CH$_2$, NH, S or O; l represents an integer of 0 to 5; m and n each independently represent an integer of 0 to 5;
the sum of m and n is not more than 5; and each organic group may be substituted by at least one or more kinds of substituents selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanate, trifluoromethyl, trifluoromethoxy and methylenedioxy;
$R^6$ represents hydrogen, and $R^7$ represents hydrogen, hydroxy, $C_1$-$C_5$ alkoxy or $C_1$-$C_5$ alkanoyloxy; or $R^6$ and $R^7$ together represent —O—, —CH2— or —S—;
$R^8$ represents hydrogen, $C_1$-$C_5$ alkyl or $C_1$-$C_5$ alkanoyl;
both $R^{12}$ and $R^{13}$ represent hydrogen; one of these represents hydrogen and the other represents hydroxy; or these together represent oxo;
Formula (II) includes (+), (−) and (±) isomers,
or a pharmacologically acceptable acid addition salt thereof.

Among the compounds represented by Formula (II) or pharmacologically acceptable acid addition salts thereof, a compound of the already shown Formula (I) or a pharmacologically acceptable acid addition salt thereof is preferably contained as an effective ingredient in the therapeutic or prophylactic agent for cachexia.

The double line consisting of a broken line and a solid line in Formula (I) represents a double bond or a single bond, and it is preferably a single bond.

$R^1$ in Formula (I) represents $C_4$-$C_7$ cycloalkylalkyl. Among those, cyclopropylmethyl, cyclobutylmethyl, cyclopentylmethyl and cyclohexylmethyl are preferred as $R^1$, and cyclopropylmethyl is especially preferred.

$R^2$ represents $C_1$-$C_5$ linear or branched alkyl. Among those, methyl, ethyl and propyl are preferred as $R^2$, and methyl is especially preferred.

B represents —CH=CH—. As B, —CH=CH— in trans-form is preferred.

As a compound represented by Formula (I), the compound in (−) isomer, wherein R¹ is cyclopropylmethyl, R² is methyl, and B is —CH=CH— in trans-form, that is, (−)-17-(cyclopropylmethyl)-3,14β-dihydroxy-4,5α-epoxy-6β-[N-methyl-trans-3-(3-furyl)acrylamido]morphinan:

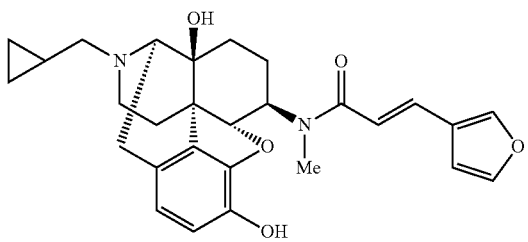 [SMILES: CN(C(=O)/C=C/c1ccoc1)[C@@H]1CC[C@@]2(O)[C@H]3Cc4ccc(O)c5c4[C@@]2(CCN3CC2CC2)[C@H]1O5]

is especially preferred.

Compounds represented by Formula (I) or pharmacologically acceptable acid addition salts thereof can be produced in accordance with the method described in WO 93/015081.

Among those compounds represented by Formula (II), the compounds in which both $R^{12}$ and $R^{13}$ represent hydrogen can be produced in accordance with the method described in PCT WO93/015081. Furthermore, the compounds in which $R^{12}$ and $R^{13}$ together represent oxo can be produced in accordance with the methods described in Chem. Pharm. Bull., 52, 664-669 (2004) and PCT W093/015081 from a compound, as a starting material, which can be produced in accordance with the methods described in, for example, Heterocycles, 63, 865-870 (2004) and Bioorg. Med. Chem. Lett., 5, 1505-1508 (1995). Moreover, the compounds in which $R^{12}$ represents hydroxy and $R^{13}$ represents hydrogen can be produced in accordance with the method described in Chem. Pharm. Bull., 52, 664-669 (2004).

Examples of "pharmacologically acceptable acid addition salts" include inorganic acid salts such as hydrochloric acid salt, sulfuric acid salt, nitric acid salt, hydrobromic acid salt, hydroiodic acid salt, phosphoric acid salt and the like; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt, phthalic acid salt and the like; organic sulfonic acid salts such as methanesulfonic acid salt, ethanesulfonic acid salt, benzenesulfonic acid salt, p-toluenesulfonic acid salt, camphorsulfonic acid salt and the like; and the like. Among those, hydrochloric acid salt, hydrobromic acid salt, phosphoric acid salt, tartaric acid salt, methanesulfonic acid salt and the like are preferably used.

"Cachexia" includes a systemic syndrome having major symptoms such as remarkable body weight loss, anemia, edema, anorexia, general prostration, malaise and the like in chronic diseases such as malignant tumor, tuberculosis, diabetes, blood diseases, endocrine disorders, infections, acquired immunodeficiency syndrome, etc. It includes, for example, cancer cachexia, tuberculous cachexia, diabetic cachexia, cachexia associated with a blood disease, cachexia associated with an endocrine disorder, cachexia associated with an infection, and cachexia associated with acquired immunodeficiency syndrome. The therapeutic or prophylactic agent is preferably used for, among those kinds of cachexia, cancer cachexia associated with malignant tumor.

"Malignant tumor" (also referred to as cancer or malignant neoplasm) includes "cancer (also referred to as carcinoma)" derived from epithelial tissue, "sarcoma" derived from non-epithelial tissue, and those derived from the hematopoietic organ. It includes, for example, malignant melanoma, malignant osteoma, stomach cancer, hepatoma, acute myeloid leukemia, acute lymphocytic leukemia, cervical cancer, uterus cancer, esophagus cancer, pancreatic cancer, prostate cancer, colon cancer, breast cancer, lung cancer, bladder cancer and ovarian cancer.

The compounds represented by Formula (I) or pharmacologically acceptable acid addition salts thereof have an ameliorating effect on cachexia, that is, an effect to ameliorate a systemic syndrome having major symptoms such as remarkable body weight loss, anemia, edema, anorexia, general prostration, malaise and the like manifested in chronic diseases such as malignant tumor, tuberculosis, diabetes, blood diseases, endocrine disorders, infections, acquired immunodeficiency syndrome and the like.

The therapeutic or prophylactic agent for cachexia is used as a therapeutic or prophylactic agent for cachexia in mammals (for example, human, mouse, rat, rabbit, dog, cat, cattle, horse, swine, monkey and the like).

The compounds represented by Formula (I) or pharmacologically acceptable acid addition salts thereof are purified to quality levels suitable for medical application and, after passing a safety test, each of the compounds and acid addition salts thereof can be orally or parenterally administered as it is or as a pharmaceutical composition in admixture with a known pharmacologically acceptable acid(s), carrier(s), vehicle(s) and the like. A dosage form can be selected for oral administration from tablets, capsules, orodispersible tablets, powders, granules and the like; for parenteral administration from intravenous bolus injection, intravenous continuous infusion, intramuscular injection, subcutaneous injection, intradermal injection, tapes, patches and the like.

The content of the compounds represented by Formula (I) or pharmacologically acceptable acid addition salts thereof in a pharmaceutical composition is not particularly limited, and the pharmaceutical composition can be formulated generally to contain 0.1 µg to 100 mg of any of the compounds and acid addition salts thereof per single dose. Furthermore, the dose of administration can be appropriately chosen depending upon the symptoms, age, sex and body weight of the patient, and its method of administration and the like, and the dose of the compounds represented by Formula (I) or pharmacologically acceptable acid addition salts thereof to be administered daily to an adult human is typically 0.1 µg to 20 mg, preferably 1 µg to 10 mg, more preferably 1 µg to 40 µg, which may be administered in a single dose or in separate doses.

As the therapeutic or prophylactic agent, any of the compounds represented by Formula (I) or pharmacologically acceptable acid addition salts thereof may be administered either alone or in combination with one or more agents used for treatment or prevention of diseases, or for alleviation or reduction of symptoms. The agents to be combined may be low molecular weight compounds, or high molecular weight proteins, polypeptides, antibodies or vaccines, etc. In this case, the agent(s) in combination can be administered simultaneously with the compound or acid addition salt thereof, or they can be administered sequentially with intervening time intervals. As a combination method, each agent may be used in combination or a drug combination may be formulated. The dose of the combined agents to be administered can be appropriately chosen based on the clinical dose of each agent. Furthermore, a combining ratio of the therapeutic or prophylactic agent for cachexia and the agents to be combined can be appropriately chosen depending upon the subject of administration; the age, body weight and symptoms of the subject of administration; the period of administration, their dosage forms, their methods of administration, the combination of drugs, and the like.

The therapeutic or prophylactic agent can be used in combination with chemotherapeutic agents, immunotherapeutic agents, diuretic agents and the like.

Examples of the chemotherapeutic agents include alkylating agents such as cyclophosphamide, ifosfamide, melphalan, busulfan, nimustine, ranimustine, temozolomide and the like; antimetabolites of nucleic acid metabolism such as methotrexate, fluorouracil, tegafur, carmofur, doxifluridine, capecitabine, cytarabine, ancitabine, enocitabine, cytarabine ocfosfate, gemcitabine, mercaptopurine, fludarabine and the like; antitumor antibiotics such as doxorubicin, daunorubicin, pirarubicin, epirubicin, idarubicin, mitoxantrone, mitomycin C, bleomycin, peplomycin and the like; microtubule inhibitors such as vincristine, vinblastine, vindesine, vinorelbine, paclitaxel, docetaxel and the like; platinum-based drugs such as cisplatin, carboplatin, nedaplatin and the like; topoisomerase inhibitors such as irinotecan, nogitecan, etoposide and the like; molecular targeted therapeutic agents such as trastuzumab, rituximab, imanitib and the like; or the like.

Examples of the immunotherapeutic agents include muramyl dipeptide derivatives, lentinan, sizofiran, ubenimex, picibanil, krestin, interferon, interleukin, granulocyte colony stimulating factor, erythropoietin and the like.

Examples of the diuretic agents include xanthine derivative drugs such as theobromine sodium salicylate; thiazide drugs such as ethiazide, cyclopenthiazide, trichlormethiazide, hydrochlorothiazide, hydroflumethiazide, benzyl hydrochlorothiazide, penflutizide, polythiazide, methyclothiazide; anti-aldosterone drugs such as spironolactone, triamterene and the like; carbonic anhydrase inhibitors such as acetazolamide and the like; chlorobenzene sulfonamide drugs such as chlortalidone, mefruside, indapamide and the like; azosemide, isosorbide, ethacrynic acid, piretanide, bumetanide, furosemide and the like.

The effectiveness of the compounds represented by Formula (I) or pharmacologically acceptable acid addition salts thereof in the treatment or prevention of cachexia, which are effective ingredients of the therapeutic or prophylactic agent for cachexia, can be evaluated by the effects thereof as described in Examples to prolong the lifetime or to suppress the body weight loss and the like in cancer-bearing animals.

EXAMPLES

Our therapeutic agents and methods will be described hereinafter by way of Examples. However, this disclosure shall not be limited to the Examples.

Example 1

The life-prolonging effect and suppressive effect on body weight loss of (−)-17-(cyclopropylmethyl)-3,14β-dihydroxy-4,5α-epoxy-6β-[N-methyl-trans-3-(3-furyl)acrylamido]morphinan hydrochloride (Compound 1) in a cachexia model Compound 1

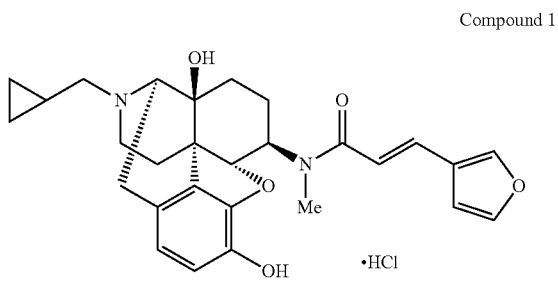 [SMILES: CN(C(=O)/C=C/c1ccoc1)[C@@H]1CC[C@@]2(O)[C@H]3Cc4ccc(O)c5c4[C@@]2(CCN3CC2CC2)[C@H]1O5 ; Cl]

The therapeutic effect of Compound 1 on cachexia was studied using an animal model of cachexia, the C57BL/6 mouse line transplanted with B16-F10 melanoma cells. Morphine and CI-977 were employed as comparison controls. Morphine is an analgesic widely used for the treatment of cancer pain and is a compound having a morphinan skeleton similar to that of our compounds, while CI-977 as well as our compound is a kappa opioid receptor agonist compound (Br. J. Pharmacol, 101, 183-189 (1990)).

C57BL/6 mice transplanted with B16-F10 melanoma cells develop the symptoms of cachexia such as body weight loss, reduced amount of movement and the like as the tumor grows. The effect of each kind of compound on the symptoms of cachexia, which was caused by B16-F10 melanoma cells, was measured by survival rate and percent change in body weight as indicators.

1. Experimental Methods

Subculture of B16-F10 melanoma cells was performed using RPMI1640 medium containing 10% FCS. For drug evaluation, 4-week-old male C57BL/6 mice (Japan SLC, Inc.) were purchased and used after 3-week acclimatization. Preparation of animal model of cachexia was performed as follows: $4 \times 10^5$ B16-F10 melanoma cells per mouse were transplanted into a footpad of a mouse; it was verified 3 weeks after transplantation that the tumor volume had increased to some extent, and thus an animal model of cachexia was obtained. Also, the tumor volume was measured for each transplanted mouse and the mice were divided into several groups such that the average tumor volume of each group would become equal. The evaluation of the therapeutic effects on cachexia was performed as described below.

Figure 2:
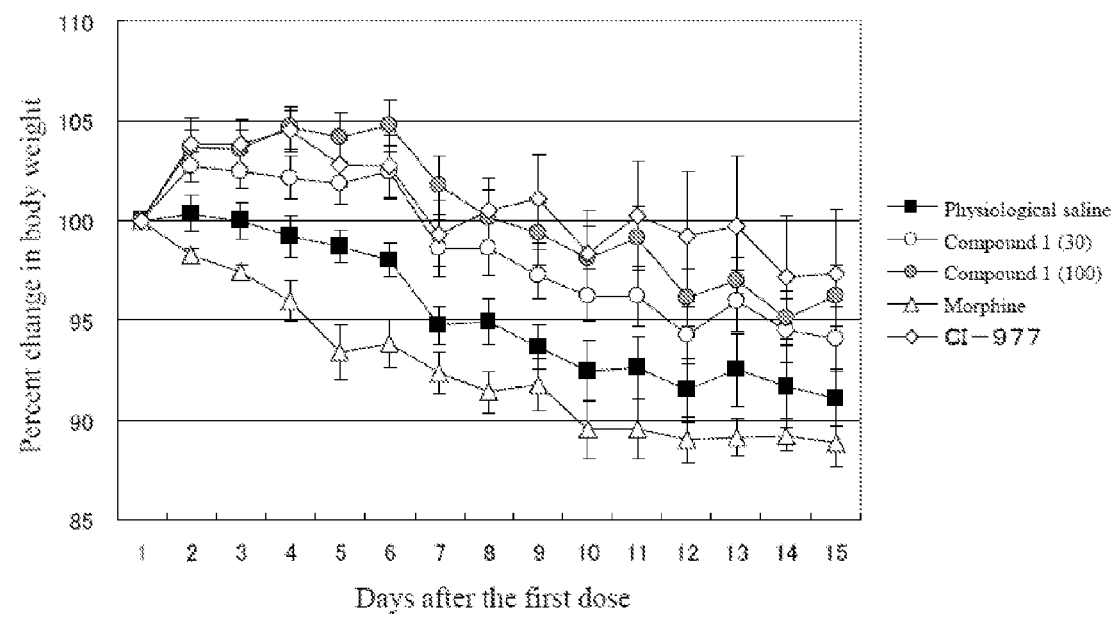
FIG. 2 shows the therapeutic effect of Compound 1 on cachexia (suppressive effect on body weight loss).

In the analyses of each kind of compound for the life-prolonging effect and suppressive effect on body weight loss, each kind of compound was administered daily (the day of first administration was considered day 1; the compounds were not administered only on day 16) to the animal models after the grouping (3 weeks after the transplantation of the cells), and the lifetime and change in body weight of each animal model was observed. The dose of each kind of compound was as follows: 30 and 100 μg/kg for Compound 1 (n=19, respectively; the numerical values in the parentheses shown in Figures indicate the doses), 5 mg/kg for morphine (n=11), 100 μg/kg for CI-977 (n=11). Physiological saline as a control was administered to animal models (n=19) in the same manner. The results observed until all the subjects died (day 57) were used to analyze the life-prolonging effect. Survival rate (%) indicates a ratio (%) of animals alive at each time point to all animals at the start of administration. Furthermore, the results observed until day 15 were used to analyze the suppressive effect on body weight loss. Percent change in body weight indicates a body weight at each time point expressed in percent, where the body weight on day 1 is defined as 100%. The results of the observation were shown in FIGS. 1 and 2.

2. Results

A statistically significant life-prolonging effect was demonstrated by administration of Compound 1 in comparison with the lifetime of the group administered with physiological saline (p=0.0335, estimation of survival curves by Kaplan-Meier method and comparison by log-rank test). In contrast, administration of CI-977 and morphine showed a tendency to reduce the lifetime. A statistically significant suppressive effect on body weight loss was demonstrated by administration of Compound 1 and CI-977 in comparison with the body weight loss in the group administered with physiological saline (p=0.0365 for 30 μg/kg of Compound 1, p=0.0007 for 100 μg/kg of Compound 1, p=0.0009 for CI-977; multiple comparisons over time (Dunnett's comparison)), while administration of morphine showed a tendency of further body weight loss.

Thus, the compounds of Formula (I), as represented by Compound 1, or pharmacologically acceptable acid addition salts thereof demonstrated effects on both life prolongation and suppression of body weight loss, indicating the effectiveness as a therapeutic or prophylactic agent for cachexia.

The invention claimed is:

1. A method of treating cachexia comprising administering a therapeutically effective amount of a compound of Formula (I):

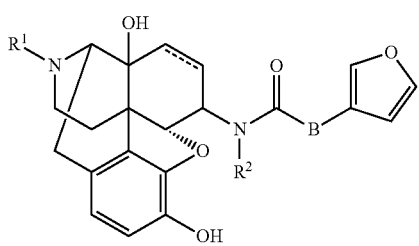

to a patient, wherein a double line consisting of a broken line and a solid line represents a double bond or single bond, $R^1$ represents $C_4$-$C_7$ cycloalkylalkyl, $R^2$ represents $C_1$-$C_5$ linear or branches alkyl, and B represents —CH=CH— or a pharmacologically acceptable acid addition salt thereof.

2. The method according to claim 1, wherein $R^1$ is cyclopropylmethyl, cyclobutylmethyl, cyclopentylmethyl or cyclohexylmethyl, and $R^2$ is methyl, ethyl or propyl.

3. The method according to claim 1, wherein $R^1$ is cyclopropylmethyl, $R^2$ is methyl, and B is —CH=CH— in trans-form.

4. The method according to claim 1, wherein the compound of Formula (I) is (−)-17-(cyclopropylmethyl)-3,14β-dihydroxy-4,5α-epoxy-6β-[N-methyl-trans-3-(3-furyl)acrylamido]morphinan:

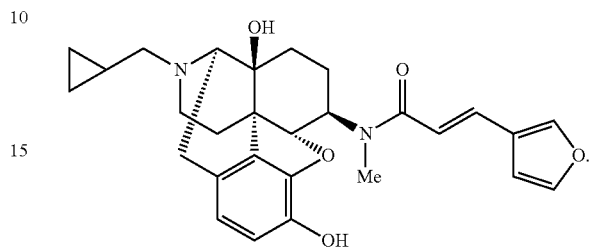

5. The method according to claim 1, wherein the cachexia is cancer cachexia.

6. The method according to claim 2, wherein the cachexia is cancer cachexia.

7. The method according to claim 3, wherein the cachexia is cancer cachexia.

8. The method according to claim 4, wherein the cachexia is cancer cachexia.

* * * * *